US011783228B2

(12) United States Patent
Harrivel et al.

(10) Patent No.: US 11,783,228 B2
(45) Date of Patent: Oct. 10, 2023

(54) SYSTEM AND METHOD FOR HUMAN OPERATOR AND MACHINE INTEGRATION

(71) Applicant: UNITED STATES OF AMERICA AS REPRESENTED BY THE ADMINISTRATOR OF NASA, Washington, DC (US)

(72) Inventors: Angela R. Harrivel, Poquoson, VA (US); Chad L. Stephens, Poquoson, VA (US); Kellie D. Kennedy, Poquoson, VA (US); Alan T. Pope, Poquoson, VA (US)

(73) Assignee: UNITED STATES OF AMERICA AS REPRESENTED BY THE ADMINISTRATOR OF NASA, Washington, DC (US)

(*) Notice: Subject to any disclaimer, the term of this patent is extended or adjusted under 35 U.S.C. 154(b) by 52 days.

(21) Appl. No.: 17/307,639

(22) Filed: May 4, 2021

(65) Prior Publication Data
US 2021/0256425 A1   Aug. 19, 2021
US 2022/0318673 A9   Oct. 6, 2022

Related U.S. Application Data

(63) Continuation of application No. 15/908,026, filed on Feb. 28, 2018, now Pat. No. 10,997,526, which is a (Continued)

(51) Int. Cl.
*G09B 5/00* (2006.01)
*G06N 20/00* (2019.01)
*G06N 5/04* (2023.01)
*A61B 5/18* (2006.01)
*G06F 3/01* (2006.01)
(Continued)

(52) U.S. Cl.
CPC .............. *G06N 20/00* (2019.01); *A61B 5/18* (2013.01); *A61B 5/7264* (2013.01); *A63F 13/212* (2014.09); *A63F 13/42* (2014.09); *A63F 13/67* (2014.09); *G06F 3/011* (2013.01); *G06F 3/015* (2013.01); *G06N 5/04* (2013.01); *G09B 5/00* (2013.01); *A61B 5/0022* (2013.01); *A61B 5/0075* (2013.01); *A61B 5/021* (2013.01); *A61B 5/0816* (2013.01); *A61B 5/318* (2021.01); *A61B 5/369* (2021.01); *A61B 5/389* (2021.01); *A63F 13/21* (2014.09); *A63F 13/428* (2014.09); *G06F 2203/011* (2013.01)

(58) Field of Classification Search
CPC ........... A61B 5/18; G06N 5/04; A63F 13/428; G09B 5/00
USPC ........................................... 434/247
See application file for complete search history.

(56) References Cited

U.S. PATENT DOCUMENTS

| 2003/0139654 | A1* | 7/2003 | Kim .................. | A61B 5/16 600/300 |
| 2009/0082692 | A1* | 3/2009 | Hale ................. | A61B 5/16 600/301 |

* cited by examiner

*Primary Examiner* — Thomas J Hong
(74) *Attorney, Agent, or Firm* — Shawn P. Gorman; M. Bruce Harper; Trenton J. Roche (57) ABSTRACT

Aspects of the present disclosure are directed to devices, systems, and methods for optimized integration of a human operator with a machine for safe and efficient operation. Accordingly, aspects of the present disclosure are directed to systems, methods, and devices which evaluate and determine a cognitive state of an operator, and allocate tasks to either the machine and/or operator based on the cognitive state of the operator, among other factors.

9 Claims, 5 Drawing Sheets

Related U.S. Application Data continuation-in-part of application No. 15/490,130, filed on Apr. 18, 2017, now Pat. No. 10,192,173, which is a continuation-in-part of application No. 14/212,159, filed on Mar. 14, 2014, now Pat. No. 9,623,324, which is a continuation-in-part of application No. 13/166,166, filed on Jun. 22, 2011, now Pat. No. 8,827,717.

(60) Provisional application No. 62/465,223, filed on Mar. 1, 2017, provisional application No. 61/781,355, filed on Mar. 14, 2013, provisional application No. 61/499,733, filed on Jun. 22, 2011, provisional application No. 61/361,084, filed on Jul. 2, 2010.

(51) Int. Cl.
| | | |
|---|---|---|
| *A61B 5/00* | (2006.01) | |
| *A63F 13/212* | (2014.01) | |
| *A63F 13/67* | (2014.01) | |
| *A63F 13/42* | (2014.01) | |
| A63F 13/21 | (2014.01) | |
| A63F 13/428 | (2014.01) | |
| A61B 5/08 | (2006.01) | |
| A61B 5/021 | (2006.01) | |
| A61B 5/318 | (2021.01) | |
| A61B 5/369 | (2021.01) | |
| A61B 5/389 | (2021.01) | |

SYSTEM AND METHOD FOR HUMAN OPERATOR AND MACHINE INTEGRATION

CROSS-REFERENCE TO RELATED PATENT APPLICATION(S)

This patent application is a continuation of co-pending U.S. application Ser. No. 15/908,026, entitled "SYSTEM AND METHOD FOR HUMAN OPERATOR AND MACHINE INTEGRATION," filed Feb. 28, 2018, which claimed the benefit of and priority to U.S. Provisional Patent Application No. 62/465,223, filed on Mar. 1, 2017, and is a continuation-in-part of, and claims the benefit of and priority to, co-pending U.S. application Ser. No. 15/490,130 entitled SYSTEM AND METHOD FOR TRAINING OF STATE-CLASSIFIERS filed Apr. 18, 2017, which is a continuation in part of and claims the benefit of and priority of: U.S. application Ser. No. 14/212,159 entitled PHYSIOLOGI-CALLY MODULATING VIDEOGAMES OR SIMULA-TIONS WHICH USE MOTION-SENSING INPUT DEVICES filed Mar. 14, 2014, which is a continuation in part of and claims the benefit of and priority to each of: U.S. patent application Ser. No. 13/166,166 entitled PHYSI-OLOGICALLY MODULATING VIDEOGAMES OR SIMULATIONS WHICH USE MOTION-SENSING INPUT DEVICES filed Jun. 22, 2011, which claims the benefit of and priority to each of U.S. Provisional Patent Application No. 61/361,084, filed Jul. 2, 2010, and U.S. Application Ser. No. 61/499,733, entitled METHOD AND SYSTEM FOR PHYSIOLOGICALLY MODULATING VIDEOGAMES WHICH USE HAND AND BODY MOTION-SENSING INPUT DEVICES filed Jun. 22, 2011; and U.S. Application Ser. No. 61/781,355, entitled METHOD AND SYSTEM FOR PHYSIOLOGICALLY MODULATING VIDEOGAMES WHICH USE HAND AND BODY MOTION-SENSING INPUT DEVICES filed Mar. 14, 2013. The entire contents of each of the foregoing applications are incorporated herein by reference in its entirety.

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefore.

BACKGROUND OF THE INVENTION

The present disclosure generally relates to the assignment of tasks to a machine and/or human operator. With increased sophistication in technology, the cognitive state of a human operator has increasingly become an important and frequently limiting factor in the proper performance of many advanced systems. For instance, attention-related human performance limiting states (AHPLS), such as channelized attention, diverted attention, inattention, high and low workload, confirmation bias, and a startled state, are significant concerns in safety critical applications, such as operation of passenger aircrafts. If an operator is in a performance limiting cognitive state, the likelihood that the operator may make an error increases and system performance and safety may degrade.

The foregoing discussion is intended only to illustrate the present field and should not be taken as a disavowal of claim scope.

BRIEF SUMMARY OF THE INVENTION

Aspects of the present disclosure are directed to devices, systems, and methods for optimized integration of a human operator with a machine for safe and efficient operation of an underlying system. Accordingly, aspects of the present disclosure are directed to systems, methods, and devices which evaluate and determine a cognitive state of an operator, and allocate tasks to either the machine and/or operator based on the cognitive state of the operator, among other factors. Aspects of the present disclosure are readily applicable to a variety of applications, such as any system, or device which utilizes or is otherwise affected by the cognitive state of an operator.

Embodiments of the present disclosure are directed to a method of task allocation in a human operator-computer interface. The method includes sampling a set of multimodal signals indicative of psycho-physiological responses of the operator over a time period. The set of multimodal signals over the period of time are then associated with one or more cognitive states of the operator. A task is then allocated to either the operator or the computer based at least in part on the one or more cognitive states of the operator. In more specific embodiments, the step of associating the set of multimodal signals with cognitive states of the operator includes classifying the multimodal signals using state-classifiers to determine the cognitive states of the operator.

In some embodiments, a system for task allocation in a human operator-computer interface is disclosed. The system comprises a set of sensors that provides a set of multimodal signals indicative of psycho-physiological responses of an operator in a first time period, and controller circuitry communicatively coupled to the set of sensors. The controller circuitry receives and analyzes the set of multimodal signals from the sensors, and classifies the multimodal signals using state-classifiers to determine the one or more cognitive states of the operator. Based at least in part on the one or more cognitive states of the operator, the controller circuitry allocates a task to either the operator or the computer. In yet more specific implementations, the controller circuitry, in response to a user input associates one or more of the cognitive states with the multimodal signals, trains the one or more state-classifiers to map the multimodal signals from the first time period to the one or more user input cognitive states.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF THE INVENTION

Aspects of the present disclosure are directed to devices, systems, and methods for optimized integration of a human operator with a machine for safe and efficient operation of an underlying system (e.g., vehicle). Accordingly, aspects of the present disclosure are directed to systems, methods, and devices which evaluate and determine a cognitive state of an operator, and allocate tasks to either an (semi-)autonomous system of a vehicle and/or an operator based on the cognitive state of the operator, among other factors. Aspects of the present disclosure are readily applicable to a variety of applications, such as any system, or device which utilizes or is otherwise affected by the cognitive state of an operator. More specifically, aspects of the present disclosure may find application in automobiles, airplanes, robots, among others.

For example, in the aerospace industry automation plays a significant role in the cockpit, and enables operators to exceed performance expectations (e.g., longer shifts, improved control, and safety). However, automation has also been associated with suboptimal psychological operator states such as complacency, boredom, diminished alertness, compromised vigilance, lapsing attention, preoccupation, and absorption. These various operator states may be indicated by covert-psychological, or psycho-physiological markers.

Vehicles outfitted with sensors and systems that facilitate varying degrees of autonomy are being developed. To improve safety in such vehicles, the human-machine interface must be optimized. Human status during operation of a vehicle is highly variable and difficult to predict. Though human operators generally have good reliability as vehicle operators, operator status of vehicles with some degree of autonomy ranges from completely incapacitated to ready to take over autonomously controlled systems if necessary. Accordingly, it is highly desirable for these vehicles to know the operator's cognitive state at any given time to facilitate allocation of tasks between the operator and the automated system in a way that maintains safe operation of the vehicle.

Operator cognitive state is a significant factor effecting efficiency and safety in operation of various systems and/or vehicles. Evaluation of cognitive state may be further useful to facilitate operator training and/or enhance operability for a number of applications. Cognitive activity is associated with various psychological and psycho-physiological responses exhibited by an operator. Cognitive state may be inferred from various sources of psycho-physiological data including, for example, sensors measuring electroencephalogram (EEG), event-related potentials (ERP), functional near infrared spectroscopy (fNIRS), electrocardiogram (EKG), heart rate, blood pressure, respiration rate, skin temperature, galvanic skin response (GSR), electromyogram (EMG), pupil dilation, eye movement, voice stress analysis (e.g., based on vocal timbre), and/or facial feature(s). Various other aspects of operator state monitoring are disclosed in U.S. Patent Publication No. 2017/0220956, which is hereby incorporated by reference in its entirety.

Some previous approaches to operator cognitive-state monitoring utilizes a single physiological measure to perform limited cognitive state evaluation. Such approaches may be useful, for example, to quantify a level of cognitive activity or cognitive workload of an operator. For example, U.S. Pat. No. 5,377,100, which is incorporated herein by reference in its entirety, describes systems and methods for evaluating a level of mental engagement in a task from an individual's electroencephalography (EEG) index of attention. As another example, U.S. Pat. No. 9,848,812 describes the detection of mental state and reduction of artifacts using fNIRS. However, a single type of physiological response may not be sufficient to distinguish between different cognitive states associated with similar levels of cognitive activity. In one or more embodiments of the present disclosure, cognitive state of an operator may be determined in real time from analysis of data and/or signals acquired from multiple different sources of psycho-physiological data. For ease of reference, a set of data and/or signals acquired from multiple different psycho-physiological sources may be referred to herein as being multimodal. Data from the individual psycho-physiological modalities may be combined to take advantage of any synergistic information they provide. Whereas a single indicator may result in a false positive or negative assessment, use of multiple indicators allows machine learning techniques and convergent validity to be leveraged in classification of cognitive states.

Evaluation of cognitive state can be challenging as psycho-physiological responses of an operator in a particular cognitive state may vary from person to person. To ensure accurate classification, state-classifiers may need to be individually trained for each operator to map the particular psycho-physiological responses of the operator to each cognitive state. In one or more embodiments, a system is configured to present stimuli to induce various target cognitive states in an operator. While presenting the stimuli, multimodal signals indicating psycho-physiological responses of the operator are sampled. One or more of the state-classifiers are trained using, for example, supervised and/or unsupervised machine learning classifier training techniques to map characteristics of the recorded psycho-physiological responses to the target cognitive state intended to be induced by the presented stimuli.

In some embodiments, one or more state-classifiers may be further refined or verified by a human cognitive state specialist. For instance, a system may be used to process the multimodal signals received from one or more psycho-physiological sensors then display the determined cognitive state to the specialist for verification and/or refinement of state-classifiers. The specialist may review/verify the system's final state determination or re-define the state to correct the state-classifiers as necessary. Specialist review may be useful, for example, when a target cognitive state may only be achieved for a small portion of the period in which stimuli was presented. For instance, an operator may be required to perform a task for some time before the operator falls into a channelized attention state. In some implementations, the system may provide a graphical user interface (GUI) for display of operational tasks and selection of correct cognitive state by a cognitive state specialist during playback. For instance, the GUI may allow a cognitive state specialist to identify portions of time in which a particular cognitive state is exhibited and/or select the cognitive state indicated by the multimodal signals and re-define the state-classifier(s) for the identified period to achieve proper identification of the state. State-classifiers may then be retrained to more accurately map the multimodal signals sampled in the identified period to the cognitive state selected by the cognitive state specialist.

Aspects of the present disclosure achieve improved safety by querying the state of the vehicle operator and making task allocation decisions based at least in part on the vehicle's trust in the operator which may, in turn, be based on the operator's state. The vehicle may further track an operator's performance in response to task allocations over time and gained/lost trust in the operator. The amount of trust in the operator may be manifested by a dynamic trust-in-human operator metric which may further be considered when allocating a task.

A method/system for optimizing operator integration and teaming with a (semi-) autonomous vehicle may determine the boundaries of physical and cognitive human behavior which support safe and efficient operation of a vehicle. Data associated with the psycho-physiological activity of the operator must then be sensed using various sensors and shared with one or more systems of the vehicle. The various vehicle systems may then access action criteria which provide guidance on the boundaries between autonomous system and human operator actions. This is especially critical during unexpected and difficult circumstances, which may result in dynamic boundaries depending on the situation. Aspects that may be considered by the vehicle systems for task allocation may include: prioritization of critical tasks, vehicle configuration, phase of flight, operator status (e.g., distracted, ready, incapacitated, ill-intentional, etc.), and skill of operator, among others. Cataloging and prioritizing critical tasks (via action criteria) may further dynamic task allocation, in the context of increasingly autonomous systems, and enhance real time task assignment.

Aspects of the present disclosure are directed to optimizing utilization of a vehicle operator by monitoring the status of the operator and communicating that information to the vehicle to facilitate task allocation to improve the safety and efficiency of operations. Existing human-machine integration suffers from over/under reliance of the operator. As disclosed herein, novel human-machine integration is accomplished by dynamically optimizing the system's reliance on the operator, further allowing for flexibility in autonomy levels and even machine-assisted skill training based on real-time operator status. Further, improved human-machine integration enables high-proficiency autonomous systems, which can reduce the number of operators required for a vehicle.

Various features are described hereinafter with reference to the figures. It should be noted that the figures are not drawn to scale and that the elements of similar structures or functions are represented by like reference numerals throughout the figures. It should be further noted that the figures are only intended to facilitate the description of the features. The figures are not intended as an exhaustive description of the claimed invention or as a limitation on the scope of the claimed invention. In addition, embodiments covered hereby need not have all the aspects or advantages shown. An aspect or an advantage described in conjunction with a particular embodiment is not necessarily limited to that embodiment and can be practiced in any other embodiments even if not so illustrated.

Figure 1A:
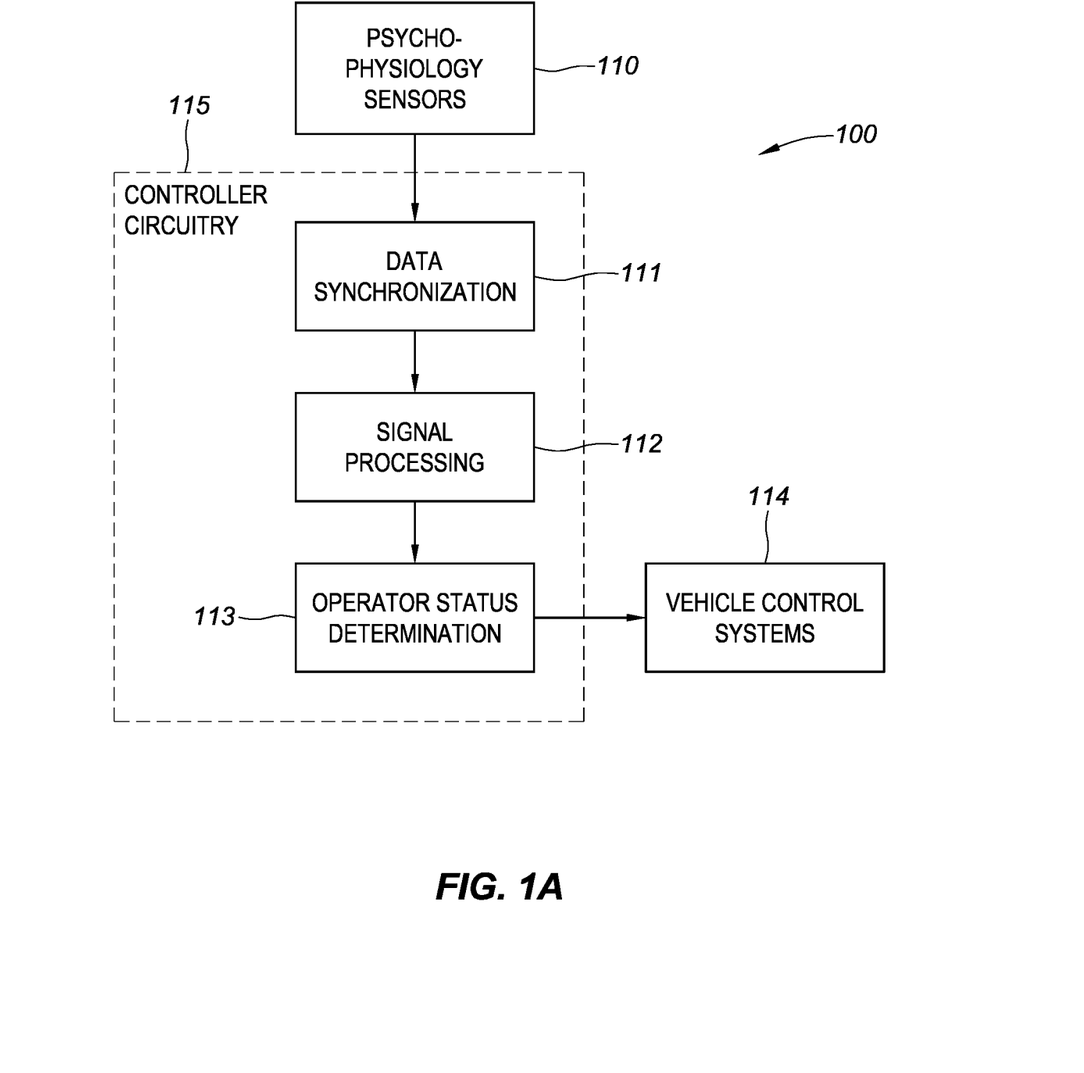
FIG. 1A is a block diagram of a system for operator status determination, consistent with various embodiments of the present disclosure.

As shown in FIG. 1A, a block diagram of a system 100 for operator status determination is disclosed. The system 100 includes psycho-physiology sensors 110 (also referred to as psycho-physiological sensors) which transmit signals indicative of various psycho-physiological indices of a vehicle operator. The data signals from each of the sensors 110 are time synchronized by a data synchronization module 111 within controller circuitry 115. Controller circuitry 115 may further include signal processing circuitry 112, which may conduct analog-to-digital conversion of the sensor signals, band-pass filtering to reduce signal noise, power spectral density (PSD) filtering, and wavelet de-noising, among other common signal processing techniques well known in the art. The processed signals are then transmitted to an operator status determination module 113, which determines a cognitive state of the operator. For example, module 113 may determine the operator distraction level and readiness to respond to and complete a task.

Vehicle control systems 114 receives the operator status from controller circuitry 115 and allocates tasks based at least in part on the operator status. In various embodiments, the vehicle may include more than one operator and the controller circuitry 115 or duplicative controller circuitry for each of the operators may provide operator status information to the vehicle control systems 114. System 114 may then allocate various pending tasks to one or more operators, and/or an autonomous system.

In some more specific embodiments, operator status determination module 113 may predict an operator's future status using historical data and known psycho-physiological operator trends (e.g., circadian rhythm).

Figure 1B:
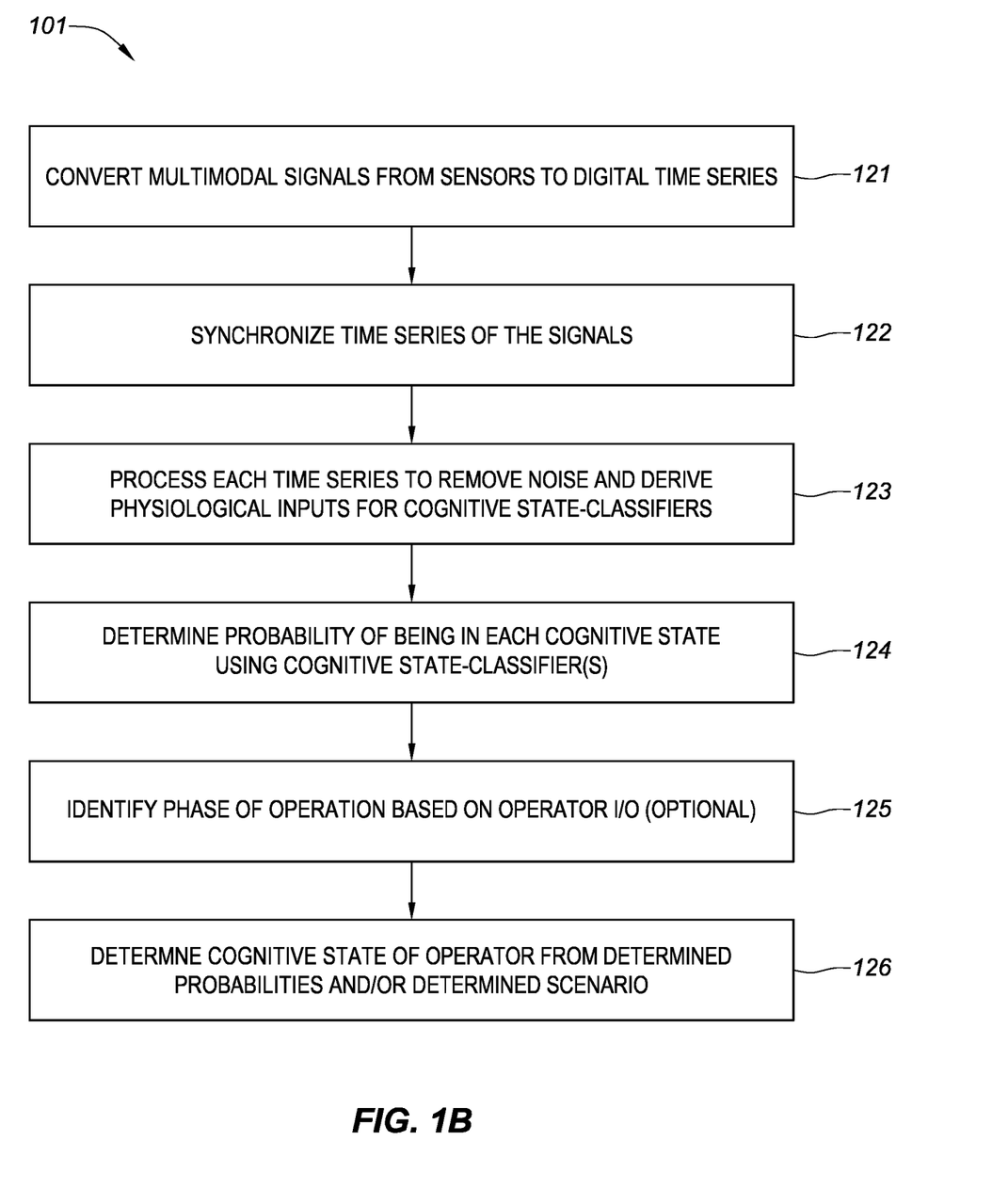
FIG. 1B is an example process for classifying a cognitive state of an operator, consistent with various embodiments of the present disclosure.

FIG. 1B is an example process 101 for classifying a cognitive state of an operator, consistent with various embodiments of the present disclosure. At block 121, analog multimodal signals from sensors are converted to digital time series (e.g., using a sampling circuit). At block 122, the digital time series are synchronized in the time domain. One or more time series may be processed at block 123 to remove noise and derive inputs for state-classifiers.

State-classifiers may be implemented using various logic structures to map multimodal signals to cognitive states. Some example logic structures that may be utilized include, but are not limited to, neural networks, evolutionary/genetic algorithms, static preprogramed functions, look up tables, or various combinations thereof. In some embodiments, classification may be performed by a plurality of state-classifiers arranged in a hierarchy having a plurality of levels. For example, a first set of state-classifiers may be each configured to output a probability that a respective cognitive state is being exhibited by an operator. A second set of classifiers may receive and evaluate the probabilities from the first set of state-classifiers, and/or other data sources, to determine the most likely cognitive state being exhibited. In this example, respective probabilities of being in each cognitive state are determined using one or more state-classifiers at block 124.

Optionally, vehicle status may be identified at block 125 using a scenario classifier. For instance, based on recorded flight data of an aircraft (e.g. recorded by a black box), it may be possible to identify vehicle status (e.g., takeoff, landing, equipment failure, etc.). Knowledge of the vehicle status may assist a state-classifier in more accurately determining an operator's cognitive state. As an illustrative example, it may be typical for a pilot (operator) to exhibit a higher heart rate during landing in comparison to flight at cruising altitude. Accordingly, a state-classifier may be trained to require a higher heart rate to classify an operator as being startled when in a landing scenario.

At block 126, the cognitive state of an operator is determined based on the determined probabilities and/or scenarios. As previously described, the cognitive state determination may be performed using one or more additional state-classifiers. For instance, one or more additional state-classifiers may adjust probabilities determined at block 124 (e.g., based on phase of vehicle operation). The additional state-classifiers may determine the most likely cognitive state based on the adjusted probabilities.

Figure 2:
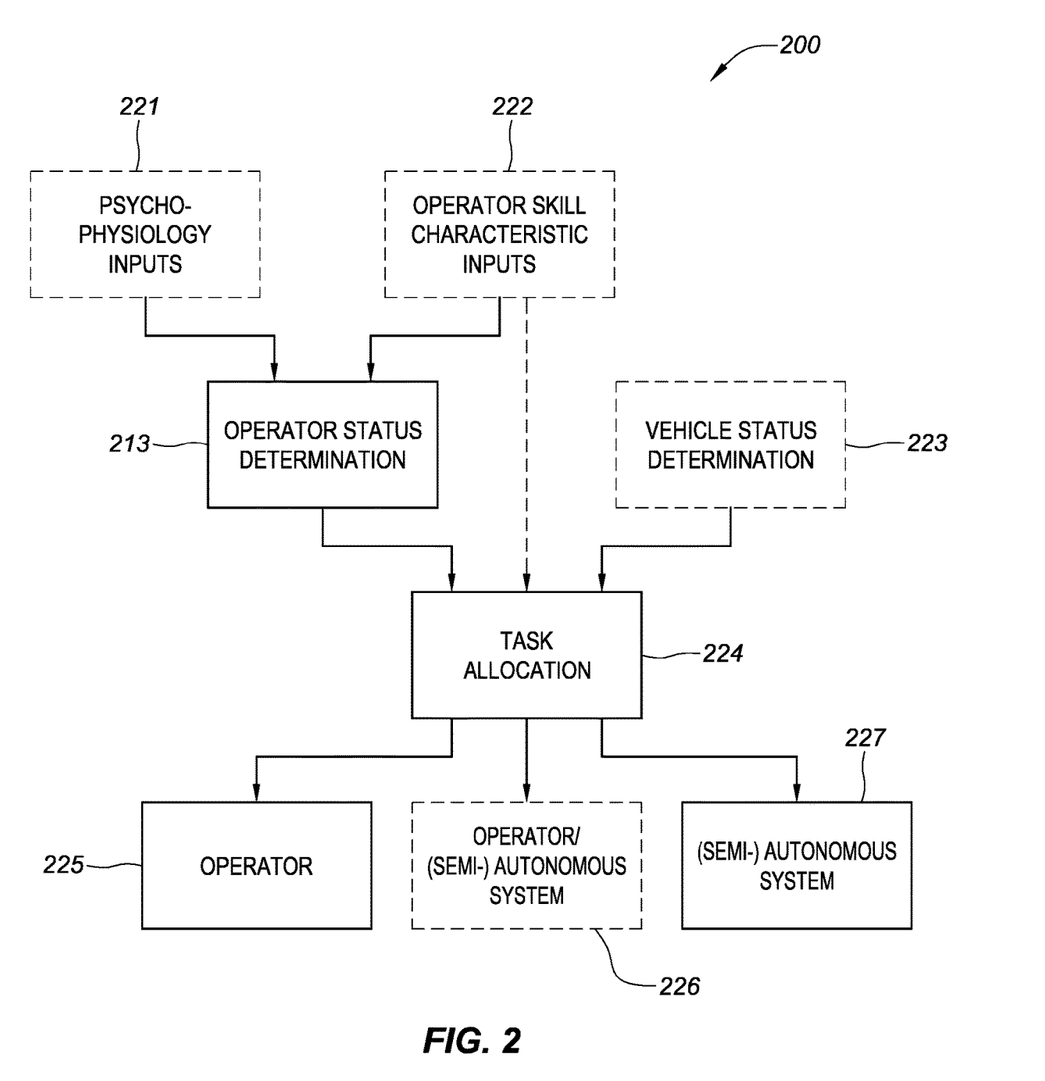
FIG. 2 is a process flow chart for operator status determination and task allocation, consistent with various embodiments of the present disclosure.

FIG. 2 is a process flow chart 200 for operator status determination and task allocation, consistent with various embodiments of the present disclosure. Operator status determination 213 may utilize inputs including psycho-physiological inputs 221 which may be received from psycho-physiological sensors communicatively coupled to an operator. Additionally, operator skill characteristic inputs 222 may be received and considered for purposes of operator status determination 213. In other embodiments, the operator skill characteristic inputs 222 may be transmitted through operator status determination 213 for consideration by task allocation 224 or may be directly communicated to task allocation 224. Operator status is then used as an input for task allocation 224. Further inputs for task allocation 224 may include vehicle status determination 223. Operator skill characteristics may include an operator's skill level in various aspects of vehicle operation. For example, the operator may be skilled at take-off, but a novice at landing. Accordingly, these characteristics may be considered when allocating tasks to the operator. A take-off related task may be assigned to the operator, while a landing related task may be assigned to another operator (if available), or to an autonomous system better suited to complete the task.

Vehicle status as determined by vehicle status determination 223 may also be a factor considered for task allocation 224. For example, vehicle configuration and stage-of-flight may affect various task allocations. During atmospheric re-entry of a vehicle, for example, a nominal task that would otherwise be allocated to an operator 225, may be tasked to an autonomous system 227 or the task allocation to the operator may be delayed until a change in stage-of-flight.

Tasks may also be dynamically reassigned based on a change in operator or vehicle status. For example, where an operator is tasked with throttling down a vehicle as the vehicle approaches maximum dynamic pressure, a change in status from focused monitoring to preoccupied may trigger a task reallocation where necessary for the safety of the vehicle. Further, operator assigned tasks may be re-assigned to an autonomous system where the operator fails to complete the task within a set period of time, or vice versa. Some tasks, such as system critical tasks, may be assigned to both operator and (semi-)autonomous system 226. In such a case, the task may be completed by either the operator or autonomous system, whichever starts/completes the task first.

It is important to note that due to the multiple inputs into both operator status determination 213 and task allocation 224, the resulting task allocations are dynamic and may be highly variable based on the specific circumstances of the operator and vehicle.

Figure 3:
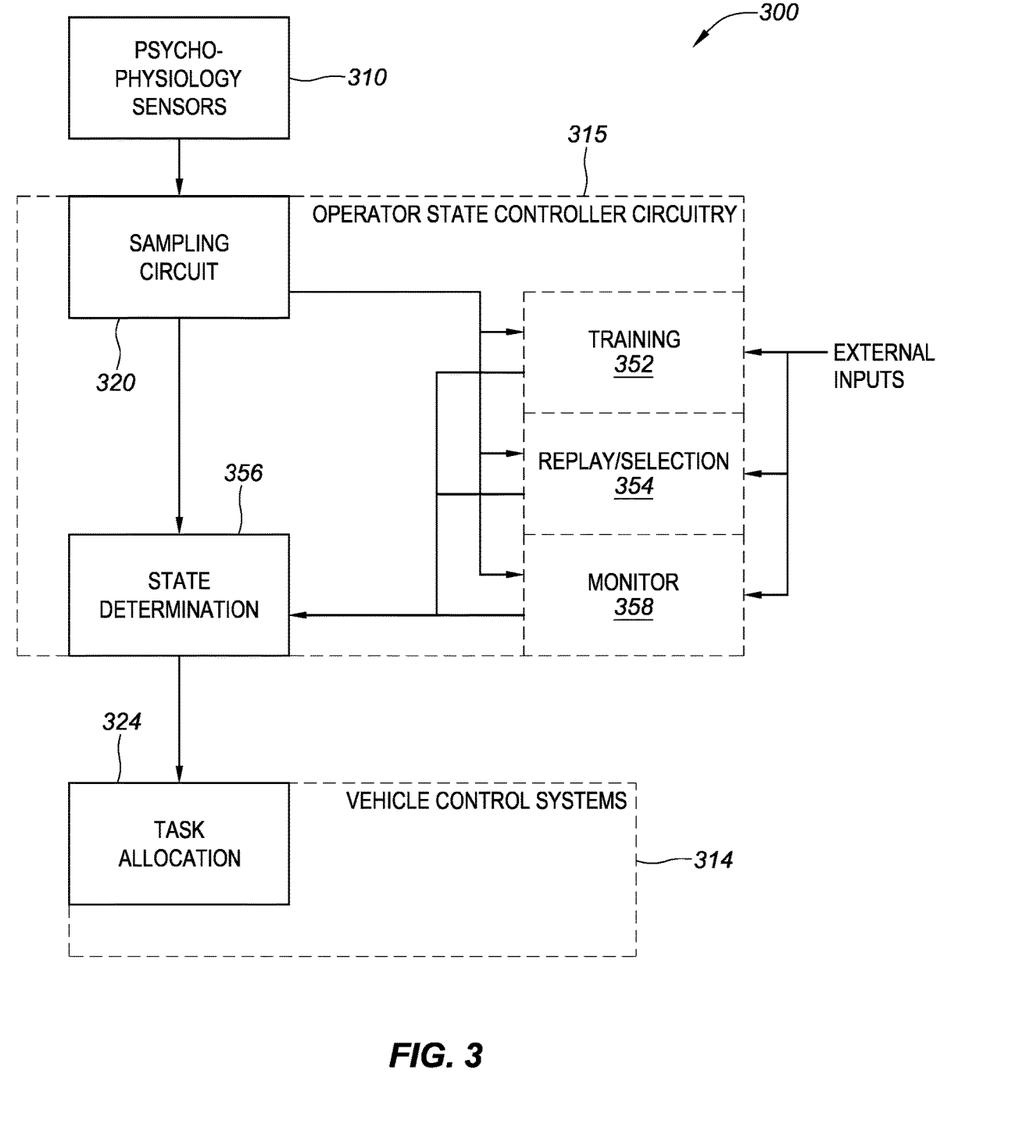
FIG. 3 is a block diagram of an environment including operator state controller circuitry and vehicle control systems which together determine an operator state and allocate a task based (at least in part) on the determined operator state, consistent with various embodiments of the present disclosure.

FIG. 3 is a block diagram 300 of an environment including operator state controller circuitry 315 and vehicle control systems 314 which together determine an operator state and allocate a task based (at least in part) on the determined operator state, consistent with various embodiments of the present disclosure. Evaluation of an operator's cognitive state may be based on an analysis of multimodal signals, which are indicative of psycho-physiological responses of the operator. These multimodal signals may then be associated with one or more state-classifiers indicative of an operator's state.

The system 300 includes a number of psycho-physiological sensors 310 that measure psycho-physiological information from an operator. In some embodiments, the psycho-physiological sensors 310 may perform a wide variety of different psycho-physiological measurements including, for example, electroencephalogram (EEG), event-related potentials (ERP), functional near infrared spectroscopy (fNIRS), electrocardiogram (EKG), heart rate, blood pressure, respiration rate, skin temperature, galvanic skin response (GSR), electromyogram (EMG), pupil dilation, eye movement, voice stress analysis (e.g., based on vocal timbre), facial feature motion detection and analysis, among others. Industry-standard methods and devices for measuring these psycho-physiological signals may, for example, be used. Examples of psycho-physiological sensors 310 include, but are not limited to, electroencephalograph, electrocardiograph, thermometer, galvanic skin response device, cardiotachometer, respiration monitor, electromyogram, imaging device and/or a microphone.

Multimodal signals produced by psycho-physiological sensors 310 are sampled by sampling circuit 320. The sampling circuit may be implemented using, for example, one or more analog to digital converters (ADCs) configured to quantize samples of analog signals provided by the sensors 310 to produce a set of digital signals. In some implementations, the sampling circuit 320 may include various other circuits for conducting signal processing of the analog and/or digital signals. Such signal processing may include, for example, amplification of signals and/or conditioning of the signals to remove noise artifacts.

Signals sampled by sampling circuit 320 are provided to operator state controller circuitry 315 for evaluation. The sampled multimodal signals are provided directly to the controller circuitry 315. Alternatively, the sampling circuit may store the sampled multimodal signals (e.g., in data storage) for later retrieval and analysis by the controller circuitry 315. The controller circuitry 315 may further receive external inputs through one or more modules 352, 354, and 358 (training module 352, replay/selection module 354, and monitor module 358). These modules may facilitate evaluation of the multimodal signals from the psycho-physiological sensors 310. In this example, training module 352 facilitates training of state-classifiers (e.g., stored in data storage) based on a set of sampled multimodal signals (e.g., using supervised and/or unsupervised learning techniques). A replay/display module 354 facilitates replay/display of operation and/or selection of a correct cognitive state. A cognitive state specialist may review the multimodal signals received from the sensors 310 and select a correct cognitive state determination. This correction may then be used to further train the state-classifiers which are used by state determination module 356 to select the appropriate state of the operator.

In the present embodiment, a state determination module 356 evaluates a cognitive state of the operator by analyzing the multimodal signals sampled by sampling circuit 320 and associating the sampled signals with one or more (trained) state-classifiers. The state determination module 356 may be implemented differently in various embodiments depending on the way in which state-classifier(s) are defined, implemented, and re-trained as necessary. In some implementations, the module 356 may receive, buffer, and input sampled multimodal signal data to a single state-classifier and store output data in a data storage device communicatively coupled thereto. In some other implementations, the module 356 may receive, buffer, and input sampled multimodal data to a plurality of different state-classifiers and make a cognitive state determination based on a comparison of the data output and the state-classifiers. For example, in one or more applications, the state determination module 356 may utilize a respective state-classifier for evaluation of each cognitive state. The module 356 may use the state-classifiers to determine the respective probabilities that the operator is in each of the cognitive states. The module 356 may then make a cognitive state determination based on the determined probabilities.

In some embodiments, controller circuitry 315 may also be configured to implement a monitor module 358 configured to monitor the cognitive state determination of the state determination module 356, and trigger various actions in response to the determined cognitive state. For instance, in some applications the module 358 may trigger various actions in response to the cognitive state and/or multimodal signals satisfying a set of action criteria. The action criteria to be performed may be specified for example in a settings file stored in data storage communicatively coupled to system 300. As an illustrative example, the monitor module 358 may be configured to generate an audible alert in response to an operator exhibiting a performance limiting state (e.g., an inattentive or channelized state).

As another example, monitor module 358 may be configured to evaluate confidence in the cognitive state determination by the state determination module 356, and trigger retraining of the state-classifiers (e.g., by training module 352) in response to the confidence level being less than a threshold value. Additionally or alternatively, state-classifiers may be adjusted on the fly to compensate for differences in responsiveness or accuracy of different sensors 310 (e.g., difference between sensors used for training and sensors in vehicle being operated). For instance, multimodal signals sampled in a baseline cognitive state may be used to recalibrate sensors to match a set of average values for the operator.

As another example, monitor module 358 may trigger an alert or display particular information (e.g., to an instructor during a training session, or to a medical technician monitoring the operator during a mission). Such information may include, for example, sampled multimodal signals, cognitive state probabilities, and/or data metrics summarizing analysis thereof. Such information may be useful, for example, to aid in assessment of training performance, providing instructional feedback, or to override a state determination of the state determination module 356.

As yet another example, a monitor module 358 may adjust a training program of a simulator based on the cognitive state determinations. For instance, in some implementations, the module 358 may prompt a simulator to provide cognitive-state based feedback to an operator. Such feedback may help to train an operator to recognize when they have entered a performance limiting cognitive state. Additionally or alternatively, the module 358 may prompt the simulator to provide positive reinforcement when good cognitive states are observed. For instance, the simulator may be prompted to provide a reward (e.g., reduced simulation time) in response to the operator recovering from a performance limiting cognitive state or in response to the operator maintaining an effective cognitive state for a requisite time period.

An operator state may be output from state determination module 356 to vehicle control systems 314 including task allocation module 324. Based at least in part on the determined operator state, the task allocation module 324 may assign tasks to either the operator or an autonomous system.

In various embodiments, the system 300 may be implemented using various technologies including, for example, software running on a general-purpose processor, dedicated hardware with application specific integrated circuits (ASICs), or by programmable integrated circuits (e.g., field programmable gate arrays) having programmable circuits configured to form circuits for performing the various module tasks. Moreover, the processing circuit may be configured to implement one or more of the modules 352, 354, 356, or 358 individually or in various combinations. Where the processing circuit is configured to implement multiple ones of the modules, the respective modules may be performed by separate sub-circuits within the processing circuit, or by one or more shared circuits within the processing circuit.

In some specific applications, system 300 may include various hardware or software components in addition to those depicted in FIG. 3. Conversely, in some embodiments, the system 300 may omit one or more components shown in FIG. 3. For example, in some embodiments, multimodal signals may be sampled and conditioned by a first system and communicated to a different system for processing. Each of these respective systems may be remotely located relative to one another.

Figure 4:
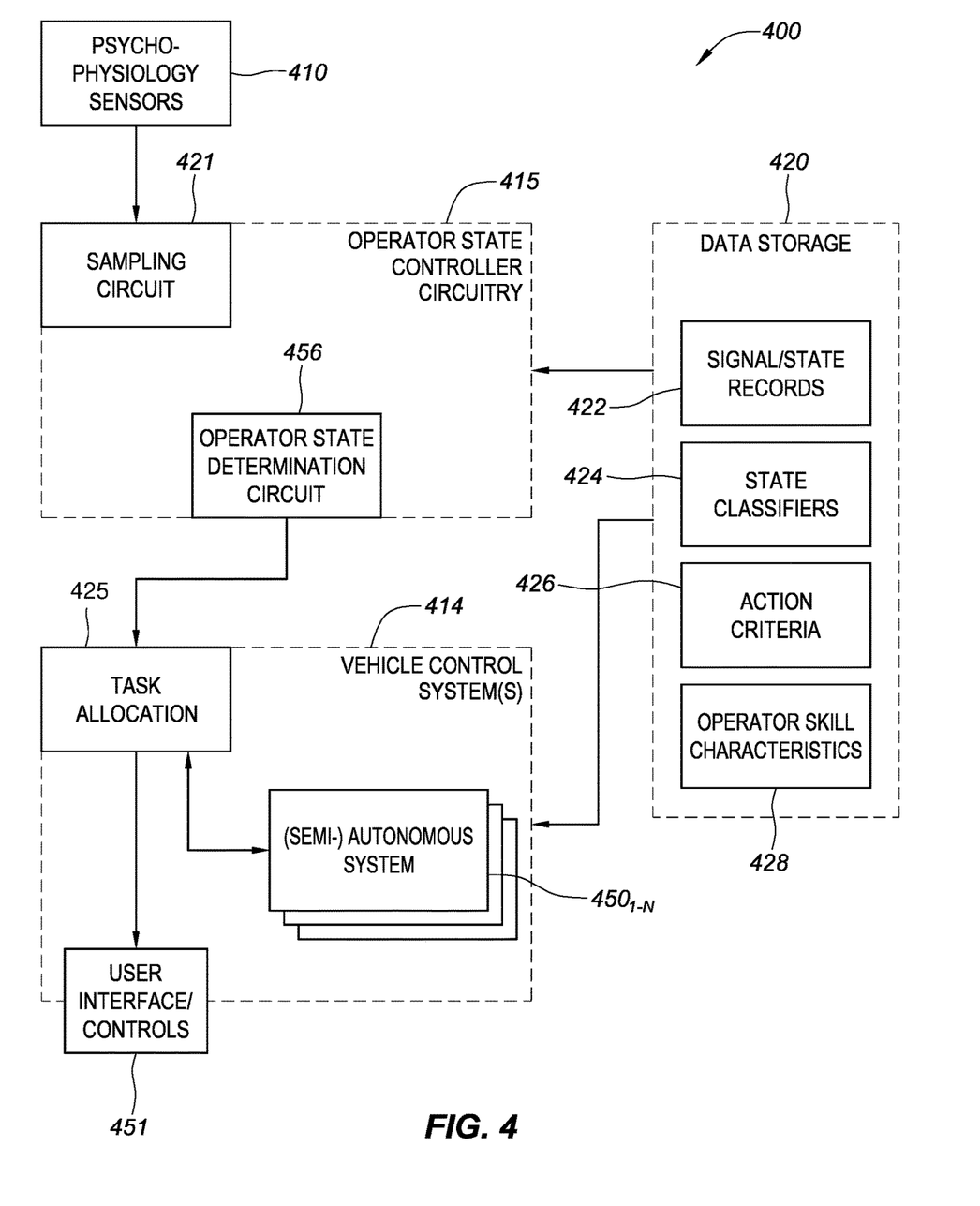
FIG. 4 is a block diagram of a system for operator state determination and task allocation based (at least in part) on the determined operator state, consistent with various embodiments of the present disclosure.

FIG. 4 is a block diagram 400 of a system for operator state determination and task allocation based (at least in part) on the determined operator state, consistent with various embodiments of the present disclosure. The system 400 includes a sampling circuit 421 which receives and samples signals from one or more psycho-physiological sensors 410. The sampled signals are then transmitted to operator state determination circuit 456 which is configured to evaluate the sampled signals. Operator state controller circuitry 415 may access one or more state-classifiers 424 in data storage circuit 420. Data storage 420 may be internal or remote storage, which is communicatively coupled to the operator state controller circuitry 415 via either a wired or wireless communication path. The operator state determination circuit 456 determines a cognitive state of the operator based on the known, state-classifiers 424 and the sampled psycho-physiological signals. In some embodiments consistent with the present disclosure, the data storage circuit 420 also stores signal/state records 422 of the psycho-physiological signals and determined cognitive states. Based on the available information, the circuit 456 determines an operator state.

Once a time-specific operator state is determined by operator state determination circuit 456, the operator state is communicated with vehicle control system(s) 414. The vehicle control system, including a task allocation circuit 425, receives a list of tasks associated with operation of the vehicle and allocates those tasks to either an operator via user interface/controls 451 or one or more (semi-)autonomous systems $450_{1-N}$. The allocation may be based, at least in part, on the state of the operator as determined by operator state controller circuitry 415. In more specific embodiments, vehicle control system 414 may be communicatively coupled to data storage circuit 420 to facilitate access to data including action criteria 426 and/or operator skill characteristics 428. This additional information may be considered by the task allocation circuit 425 when determining allocation of the task to either the operator or an autonomous system. The action criteria 426 may include rules, which limit the task allocation circuit's determination parameters. For example, flight critical tasks may be (partially) allocated to the operator to keep a human in the control loop. Other action criteria may automatically assign certain tasks or types of tasks to an autonomous system $450_{1-N}$ regardless of operator state. Where immediate attention to a task is required and the envelope for a control input is less than the reaction time for an operator, the task may be allocated to the autonomous system 450.

A task allocation circuit 425 of a vehicle control system 414 may further request operator skill characteristic data 428 from data storage 420. The operator skill characteristic data may be used by task allocation circuit 425 to override the allocation of a task to an operator in certain situations. For example, where the operator is a novice, a difficult task may be allocated to the autonomous system 450, as opposed to the operator, to maintain safety of the vehicle. This may also facilitate embodiments where tasks are assigned to a primary operator and re-assigned to a secondary operator after a period of inactivity by the primary operator. The task may be re-assigned only to a secondary operator who has the required skills to safely complete the task. For example, a trajectory correction task may not be assigned to a payload specialist.

The action criteria 426 may further identify which tasks are allocable to an operator based on the operator's skill characteristics 428. In certain embodiments, the operator may also be granted override privileges for task allocation circuitry 425. These override privileges may be task specific or universal and may be written within data storage 420 as an action criteria 426. Accordingly, an operator may reallocate a task to an autonomous system 450 or another operator, for example.

In some embodiments, the data storage circuit 420 may also store recordings indicative of the vehicle operation (e.g., flight characteristics) from the time period in which the psycho-physiological signals were sampled. Such data may facilitate the use of predictive algorithms which allow for dynamic adjustment of the criteria for operator state determination used by operator state determination circuit 456. For example, where the vehicle experiences turbulence, the operator state determination circuit 456 may anticipate that the operator's cognitive state will shortly experience a change to an absorbed state from an active monitoring state as the operator adjusts the flight path to circumvent further turbulence.

The system 400 may also facilitate real-time and/or post-operation refinement of the state-classifiers 424. In one example, multimodal signal and cognitive state determination records 422, and/or recordings of vehicle operation characteristics are written to data storage 420 for access by, for example, a cognitive state specialist. The cognitive state specialist may review and analyze this data at a user interface 451 within a vehicle control system 414. Alternatively, this data may be remotely accessed by the cognitive state specialist. The user interface 451 may replay a depiction of vehicle operation by the operator and the synchronized psycho-physiological signals from psycho-physiological sensors 410. Where the cognitive state specialist identifies a deviation from a desired system functionality, the cognitive state specialist may adjust the state-classifiers 424 to achieve the desired result. For example, where a state-classifier is erroneously assessing the operator state as distracted, when the operator is actively monitoring the vehicle dynamics, the specialist may adjust cognitive state determination of the state-classifiers 424.

Signal/state records 422 may be retrieved from data storage 420 for training of the state-classifiers 424 by a training circuit (not shown). The training process may configure the state-classifiers 424 to more accurately map the psycho-physiological signals received from the psycho-physiological sensors 410 to the correct cognitive state of the operator. If the cognitive state determined by operator state determination circuit 456 does not match the correct cognitive state, the training circuit may adjust the state-classifiers 424 to improve the mappings. Alternatively or additionally, the correct cognitive state may be selected by a cognitive state specialist via user interface 451.

The adjustment of state-classifiers 424 may be performed using various processes known in the art for algorithmic training. As one example process, the adjustment may be performed using an evolutionary algorithmic approach in which a number of small adjustments are performed and compared to the original. Adjustments may be pseudo-random or may be selected according to a predetermined process. In a neural-network-based classifier, for example, the adjustment may change weighting or connections of one or more neural nets connected to an output for the correct cognitive state. The adjusted classifiers are then evaluated by processing a set of test data and the performance is compared to that of the original classifier. If one of the adjusted classifiers provides better mapping, it is used to replace the original classifier in the data storage 420 and is used going forward.

In some embodiments, system 400 may include a monitor circuit to monitor cognitive states determined by operator state controller circuitry 415. Additionally or alternatively, the monitor circuit may be configured to monitor the psycho-physiological signals provided to circuitry 415. In some embodiments, the monitor circuit 410 may be configured to trigger various actions in response to the multimodal signals and/or determined cognitive states satisfying a set of action criteria 426 stored in data storage 420. A particular set of action criteria 426 may be applied to: an individual operator or vehicle; one or more groups of particular operators, and/or vehicles; or fleet wide. For example, a first set of action criteria may be applied to all operators and a second set of actions may be applied to only a subset of the operators (e.g., operators in training). In this manner, action criteria can be more specifically tailored for particular applications.

In some embodiments, one or more sets of action criteria 426 may be hard-coded by the manufacturer and stored in data storage 420. Additionally or alternatively, one or more sets of action criteria 426 may be customized by an operator or other authorized user (e.g., instructor or supervisor). In some implementations, the user interface 451 provided by control system 414 may include an interface for customization of action criteria. Additionally or alternatively, in some implementations, data storage 420 may be remotely accessible for configuration of action criteria by an authorized user.

Various aspects of the present disclosure may be applied to vehicle autonomy in response to unexpected and/or difficult circumstances, or operator states including incapacitated, impaired, or non-expert operators. In such embodiments, dynamic task allocation by the vehicle system may be utilized to achieve safe and efficient control of the vehicle. In yet further embodiments, task allocation may further consider vehicle configuration and phase of flight.

Research related to the present disclosure includes: Stephens, C. L., Scerbo, M. W., and Pope, A. T. Adaptive Automation for Mitigation of Hazardous States of Awareness Chapter 26 in *The Handbook of Operator Fatigue* edited by Matthews, Desmond, Neubauer, and Hancock, Ashgate 2012; Pope, A. T., Stephens, C. L., and Gileade, K. M., Biocybernetic Adaptation as Biofeedback Training Method Chapter 5 in *Advances in Physiological Computing* edited by Fairclough and Gileade, Springer 2014; Pope A. T., Stephens C. L. (2012) Interpersonal Biocybernetics: Connecting through Social Psychophysiology, ACM International Conference on Multimodal Interaction, Santa Monica, Calif., USA, 2012; Pope, A. T., and Stephens, C. L. (2011) MoveMental: Integrating Movement and the Mental Game. Presented at CHI 2011, Brain and Body Interfaces: Designing for Meaningful Interaction, May 7-12, 2011, Vancouver, Canada. All of which are incorporated by reference as though fully disclosed herein.

This application incorporates by reference: U.S. application Ser. No. 15/490,130, filed 18 Apr. 2017; U.S. application Ser. No. 14/212,159, filed Mar. 14, 2014; U.S. application Ser. No. 13/166,166, filed Jun. 22, 2011; U.S. Provisional Application No. 61/361,084, filed Jul. 2, 2010; U.S. Provisional Application No. 61/499,733, filed Jun. 22, 2011; U.S. Application No. 61/781,355, filed Mar. 14, 2013; U.S. Pat. Nos. 9,848,812, 9,084,933; 8,858,325; 8,827,717; 8,628,333; 8,164,485; 8,062,129; 6,478,735; 6,450,820; 6,104,948; and 5,377,100 as though fully disclosed herein.

For purposes of description herein, the terms "upper," "lower," "right," "left," "rear," "front," "vertical," "horizontal," and derivatives thereof shall relate to the invention as oriented in the referenced figure. However, it is to be understood that the invention may assume various alternative orientations and step sequences, except where expressly specified to the contrary. It is also to be understood that the specific devices and processes illustrated in the attached drawings, and described in the following specification, are simply example embodiments and specific dimensions and other physical characteristics relating to the embodiments disclosed herein are not to be considered as limiting, unless the claims expressly state otherwise.

Various modules or other circuits may be implemented to carry out one or more of the operations and activities described herein and/or shown in the figures. In these contexts, a "module" is a circuit that carries out one or more of these or related operations/activities (e.g., data synchronization module, and status determination module). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A computer-implemented method of allocating a task to a human operator and/or a computer within an automated system having a human operator-computer interface, the method comprising:
   receiving, via controller circuitry, a measured set of multimodal signals from a set of psycho-physiological sensors communicatively coupled to an operator and the controller circuitry, wherein the measured set of multimodal signals is indicative of psychophysiological responses of the operator over a first time period;
   sampling the measured set of multimodal signals via a sampling circuit to thereby generate a sampled set of multimodal signals, including converting the measured set of multimodal signals to a digital time series over the first time period;
   associating the sampled set of multimodal signals over the time period with one or more cognitive states of the operator as an associated cognitive state;
   dynamically allocating a task to at least one of the operator and the computer via a task allocation circuit, the allocating based at least in part on the associated cognitive state of the operator; and
   triggering an electric signal configured to provide instructional feedback to the human operator for operating the computer, the triggering being based, at least in part, on the one or more cognitive states of the operator during at least one of the first time period and one or more cognitive states of the user during a second time period.

2. The method of claim 1, wherein the first time period overlaps at least a portion of the second time period.

3. The method of claim 1, wherein the triggering of the electric signal configured to provide instructional feedback is based entirely on the one or more cognitive states of the operator during the first time period.

4. The method of claim 1, further comprising:
   deriving a dynamic trust-in-human operator metric based on the one or more cognitive states of the operator during the first time period, and wherein the allocation of the task via the task allocation circuit is based at least in part on the dynamic trust-in-human operator metric.

5. The method of claim 4, further comprising:
   transmitting an attention alert to the operator based on, at least in part, the dynamic trust-in-human operator metric.

6. The method of claim 1, wherein the human operator-computer interface controls a vehicle, and wherein the task allocation is performed as a function of vehicle status and operator skill and the task is a first task assigned to the operator, and wherein the method further comprises:
   in response to allocating the first task to the operator, operating the vehicle in response to input received from the operator;
   dynamically allocating a second task to at least the computer via the task allocation circuit; and
   in response to allocating the second task to the computer, operating the vehicle in response to input received from the computer.

7. The method of claim 1, wherein the instructional feedback is selected from the group consisting of: audio feedback, video feedback, audio-visual feedback, tactile feedback, and combinations thereof.

8. The method of claim 7, further comprising:
   sampling a second set of multimodal signals for the second time period;
   determining respective probabilities of the operator being in the one or more cognitive states using the second sampled set of multimodal signals as an input to one or more state-classifiers; and
   allocating a second task to either the operator or the computer based on, at least in part, the respective probabilities of the one or more cognitive states of the operator in the second time period.

9. The method of claim 1, wherein the multimodal signals are received from at least a sensor selected from the group consisting of: electroencephalogram (EEG), event-related potentials (ERP), functional near infrared spectroscopy (fNIRS) device, electrocardiogram (EKG), heart rate sensor, blood pressure sensor, respiration rate sensor, skin temperature sensor, galvanic skin response (GSR) sensor, electromyogram (EMG), voice stress analysis device, facial feature sensor, and combinations thereof.

* * * * *